US012264057B2

(12) United States Patent
Bhutani et al.

(10) Patent No.: US 12,264,057 B2
(45) Date of Patent: Apr. 1, 2025

(54) SINGLE TANK CARBONATION FOR CARBONATED SOFT DRINK EQUIPMENT

(71) Applicant: PepsiCo, Inc., Purchase, NY (US)

(72) Inventors: Gurmeet Bhutani, Haryana State (IN); Rahul Sadashiv Kamble, Maharashtra (IN)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 18/474,870

(22) Filed: Sep. 26, 2023

(65) Prior Publication Data

US 2024/0092624 A1 Mar. 21, 2024

Related U.S. Application Data

(63) Continuation of application No. 16/470,105, filed as application No. PCT/US2017/066696 on Dec. 15, 2017, now Pat. No. 11,787,683.

(30) Foreign Application Priority Data

Dec. 16, 2016 (IN) .............................. 201641043035

(51) Int. Cl.
| | | |
|---|---|---|
| *B67D 1/00* | (2006.01) | |
| *B67D 1/04* | (2006.01) | |
| *B67D 1/12* | (2006.01) | |
| *G01N 21/3504* | (2014.01) | |
| *G01N 21/3577* | (2014.01) | |
| *G01N 33/14* | (2006.01) | |

(52) U.S. Cl.
CPC ............. *B67D 1/0074* (2013.01); *B67D 1/04* (2013.01); *B67D 1/12* (2013.01); *G01N 21/3504* (2013.01); *G01N 21/3577* (2013.01); *G01N 33/14* (2013.01); *B67D 2210/00125* (2013.01)

(58) Field of Classification Search
CPC .......... B67D 1/0074; B67D 1/04; B67D 1/12; B67D 2210/00125; G01N 21/3504; G01N 21/3577; G01N 33/14
See application file for complete search history.

(56) References Cited

U.S. PATENT DOCUMENTS

| 4,440,318 A | * | 4/1984 | Berger | ................. B67D 1/0074 |
| | | | | 222/397 |
| 4,804,112 A | * | 2/1989 | Jeans | ..................... B67D 1/007 |
| | | | | 261/DIG. 7 |
| 2007/0187528 A1 | | 8/2007 | Roth et al. | |
| 2016/0106136 A1 | | 4/2016 | Gordon et al. | |

FOREIGN PATENT DOCUMENTS

WO  2015055743 A1  4/2015

\* cited by examiner

*Primary Examiner* — Jason K Niesz
(74) *Attorney, Agent, or Firm* — Sterne, Kessler, Goldstein & Fox P.L.L.C.

(57) ABSTRACT

A carbonated beverage dispenser includes a tank to store carbonated water, a carbon dioxide source, and a release valve configured to release gas from the tank. The release valve may be actuated to mix the contents of the tank to increase the temperature homogeny and carbon dioxide homogeny in the tank. The tank may include sensors to monitor the temperature of the water and the amount of carbon dioxide dissolved therein.

12 Claims, 4 Drawing Sheets

SINGLE TANK CARBONATION FOR CARBONATED SOFT DRINK EQUIPMENT

CROSS REFERENCE TO RELATED APPLICATIONS

This application is a continuation of U.S. application Ser. No. 16/470,105, filed Jun. 14, 2019, which is a national stage entry of International Application No. PCT/US2017/066696, filed Dec. 15, 2017, each of which is incorporated herein by reference in its entirety.

BACKGROUND

Field

Embodiments of the present invention relate generally to beverage dispensing, including, for example, carbonated soft drink equipment.

Background

Carbonated soft drink equipment may produce soft drinks with the use of carbonation tanks. Current carbonation systems use multiple tanks to meet specifications for beverages.

BRIEF SUMMARY OF THE INVENTION

In some embodiments, a carbonated drink dispensing system includes a tank configured to hold a volume of water. The water may have carbon dioxide dissolved therein. In some embodiments, the tank may be thermally coupled to an evaporator coil. The evaporator coil may serve to remove heat from the tank and the contents contained therein. In some embodiments, the tank may be coupled to a carbon dioxide source. The carbon dioxide source may be configured to deliver carbon dioxide into the tank volume. In some embodiments, the tank may be coupled to a water source. The water source may add water into the tank volume. The water source may include a pump configured to pump water into the tank volume. In some embodiments, the tank includes a release valve configured to release gas from the tank. In some embodiments, a dispensing valve is operatively coupled to the tank to dispense a carbonated beverage from the tank.

In some embodiments, the tank includes a carbon dioxide sensor. The carbon dioxide senor may determine the amount of carbon dioxide dissolved in the water and may also determine the amount of carbon dioxide present in a space above the water. The senor may determine the amount of carbon dioxide directly or indirectly. The sensor may be, for example, an infrared emitter and an infrared receiver, In some embodiments, the release valve coupled to the tank opens when the carbon dioxide sensor determines that the level of carbon dioxide dissolved in the water is outside of a threshold range.

In some embodiments, the system may further include a syrup source. The syrup source may add syrup to the carbonated beverage dispenses from the tank. In some embodiments, the syrup source may include a syrup pipe configured to transport the syrup from the syrup source. The syrup pipe may pass through the tank to cool the syrup prior to the syrup's addition to the carbonated beverage.

In some embodiments, the tank includes a controller operatively coupled to the release valve and the sensor. The controller may actuate the release valve when a signal is received from the sensor. In some embodiments, the controller may actuate the release valve for an actuation period. The actuation period may be determined based on comparing the concentration of carbon dioxide dissolved in the water and a threshold range.

In some embodiments, the system may pump water into the tank when the amount of water in the tank is less than a pre-determined level. The release valve may open a delay time after water is added to the tank. The release valve may, additionally or alternatively, open a delay time after the dispensing valve is actuated. The delay time may be, for example, 60 seconds. In some embodiments, the release valve is opened periodically.

In some embodiments, the pump is a low pressure pump and the tank has a tank volume between, and including, 6 liters and 15 liters. The tank may have a tank pressure. The tank pressure may be between a first and a second pressure. The first pressure may be approximately 50 PSI and the second pressure may be approximately 60 PSI.

In some embodiments, no tanks are disposed within the tank volume.

In some embodiments, a method of dispensing a carbonated beverage from a carbonated beverage dispensing system includes determining a concentration of carbon dioxide dissolved in water contained in the beverage dispensing system at a first time. A release valve configured to release gas from the beverage dispensing system may be actuated to agitate the water. The concentration of carbon dioxide may be monitored while the release valve is open. The release valve may be closed when the water reaches a threshold concentration. The method may further include dispensing the water with carbon dioxide dissolved therein from the carbonated beverage dispensing system.

In some embodiments, the method includes adding carbon dioxide to the beverage dispensing system from a carbon dioxide source. The method may also include adding water to the beverage dispensing system. In some embodiments, no agitation fan is used to agitate the water.

BRIEF DESCRIPTION OF THE FIGURES

The accompanying drawings, which are incorporated herein and form part of the specification, illustrate embodiments of the present invention and, together with the description, further serve to explain the principles of the invention and to enable a person skilled in the relevant art(s) to make and use the invention.

Features and advantages of the embodiments will become more apparent from the detailed description set forth below when taken in conjunction with the drawings, in which like reference characters identify corresponding elements throughout.

DETAILED DESCRIPTION OF THE INVENTION

Figure 1:
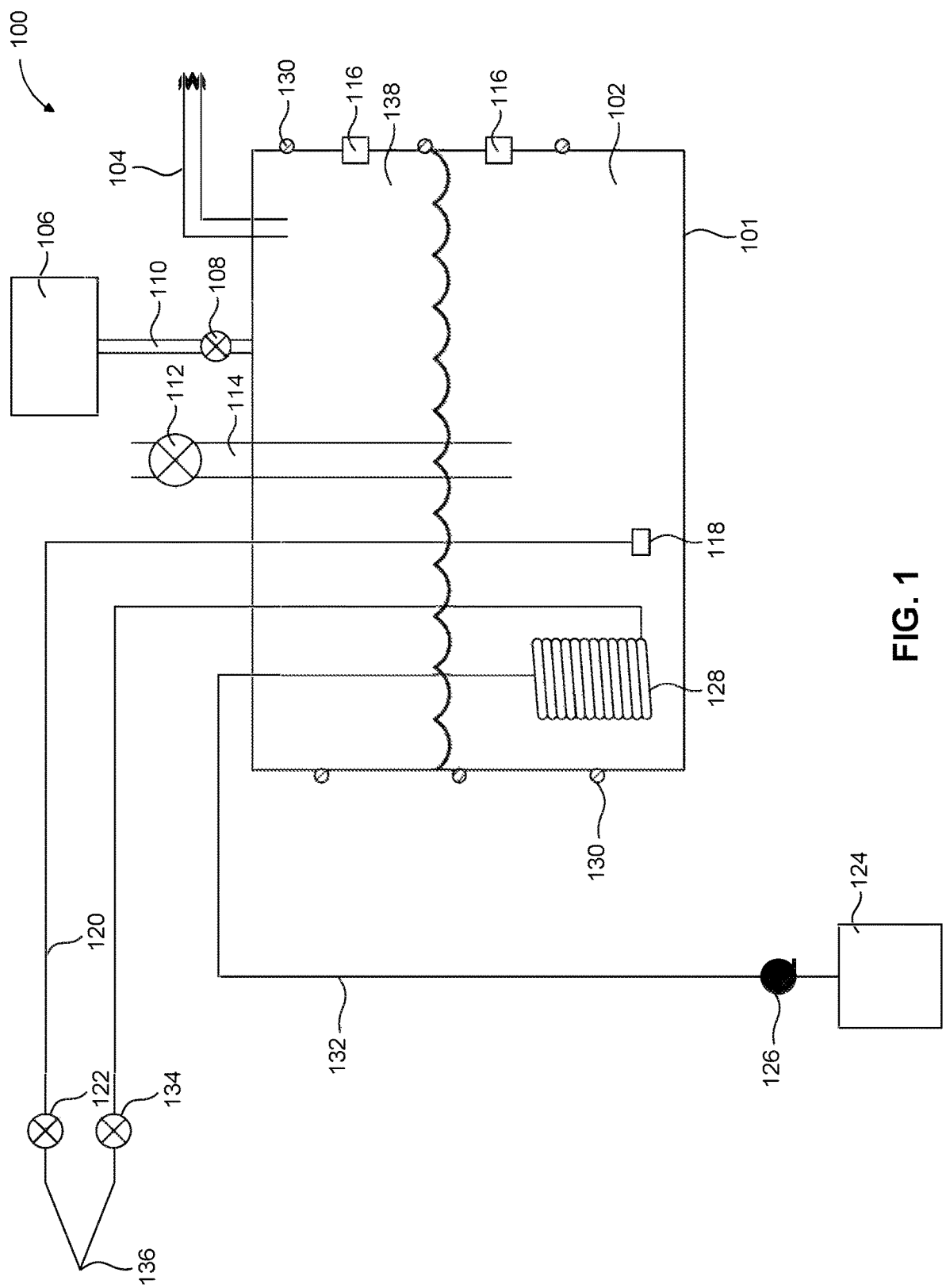
FIG. 1 shows a schematic view of a beverage dispensing system according to some embodiments.

The present invention(s) will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Carbonated beverage dispensing systems, also known as fountain drink systems, are used to dispense carbonated beverages to consumers. Carbonated beverages include carbon dioxide dissolved in water. Syrup may be added to carbonated water to produce a flavored beverage. The amount of carbon dioxide dissolved in the water contributes to the overall taste and mouthfeel of the beverage and a lack of carbonation results in a beverage that is "flat." Therefore, it is important that the water be periodically agitated to improve the homogeny of the carbon dioxide dissolved in the water and the water temperature.

In some carbonated beverage dispensers, the water is agitated using mechanical means such as an impeller. In some embodiments, the impeller may stir the water. In some embodiments, the impeller may stir the water to ensure an even distribution of a solute, such as, for example, flavoring syrup, in the water. The impeller may be activated periodically or it may be operated continuously. The use of impellers may increase the costs of operating the carbonated beverage dispensing system due to increased maintenance costs and electricity costs. Additionally, if the impeller is not operable, for example, due to a mechanical malfunction or power loss, the temperature and/or concentration of the carbonated beverage contained in the carbonated beverage dispenser may not be homogenous. The lack of homogeny may reduce the quality of the product dispensed.

Carbonated beverage dispensing systems may be tailored to specific use situations. For example, a carbonated beverage dispensing system may be designed to accommodate a constant rate of uses, for example, a use at a restaurant, or it may be designed to accommodate periodic high volume uses, for example, a use at a movie theater concession stand.

Carbonated beverage dispensing systems may use a tank to hold the water. The water may contain carbon dioxide dissolved therein. The water may be cooled using an evaporation system surrounding the tank. The evaporation system may be coupled to a refrigerant system to cool the tank. The refrigerant system may use a refrigerant such as, for example, R-134a.

These and other embodiments are discussed below with reference to the figures. However, those skilled in the art will readily appreciate that the detailed description given herein with respect to these figures is for explanatory purposes only and should not be construed as limiting.

A beverage dispensing system 100, as shown, for example, in FIG. 1, may be utilized to dispense a carbonated beverage. In some embodiments, beverage dispensing system 100 includes a tank 101. In some embodiment, tank 101 is a continuous, single walled enclosed vessel with no discrete tanks disposed therein. In some embodiments, tank 101 is configured to receive water 102 through pipe/tube 104. In some embodiments, water 102 may be flavored water or may be plain water. In some embodiments, tank 101 is configured to hold a gas 138. Gas 138 may include carbon dioxide, oxygen, nitrogen, or other gases. Water 102 contained in tank 101 may have gas 138 partially dissolved therein. In some embodiments, gas 138 and water 102 mix in tank 101 to form a carbonated water (soda)

In some embodiments, certain properties of water 102 are closely controlled or monitored. In some embodiments, properties of water 102 may include carbon dioxide concentration, temperature, and salinity. In some embodiments, the homogeny of these properties of water 102 within the tank may be important. For example, in some embodiments, it may be desirable to have the temperature of water 102 be homogenous throughout tank 101.

In some embodiments, water 102 is pumped into tank 101 via a water input pipe 104. Water input pipe 104 may be operatively coupled to a water supply such as a municipal water supply. In some embodiments, water input pipe 104 may be coupled to a water pump (not shown). In some embodiments, the water pump may be operatively coupled to other elements of the carbonated beverage dispenser 100.

In some embodiments, carbonated beverage dispenser 100 includes a carbon dioxide source 106. In some embodiments, carbon dioxide source 106 may be a cylinder or other container containing gaseous carbon dioxide. Gaseous carbon dioxide stored in carbon dioxide source 106 may be stored at a high pressure. In some embodiments, gaseous carbon dioxide is pushed at low pressure and added to tank 101 using a low pressure pump. In some embodiments, the gaseous carbon dioxide enters tanks 101 through a carbon dioxide regulator. The systems and methods of using low pressure carbon dioxide pressure may include those disclosed in commonly owned U.S. patent application Ser. No. 15/687,995, titled "LOW-PRESSURE CARBONATION FOR CARBONATED SOFT DRINK EQUIPMENT" filed Aug. 28, 2017 which is incorporated herein by reference in its entirety. Carbon dioxide source may also be, for example, a chemical carbon dioxide source such as acidic powders and bases.

In some embodiments, gaseous carbon dioxide is added to tank 101 from carbon dioxide source 106. Gaseous carbon dioxide from carbon dioxide source 106 may enter tank 101 via a carbonation pipe 110. Carbonation pipe 110 may have a carbonation input valve 108 coupled thereto. In some embodiments, carbonation input valve 108 may be a carbon dioxide pressure regulator. Carbonation input valve 108 is configured to release gaseous carbon from carbon dioxide source 106 into tank 101.

Figure 2:
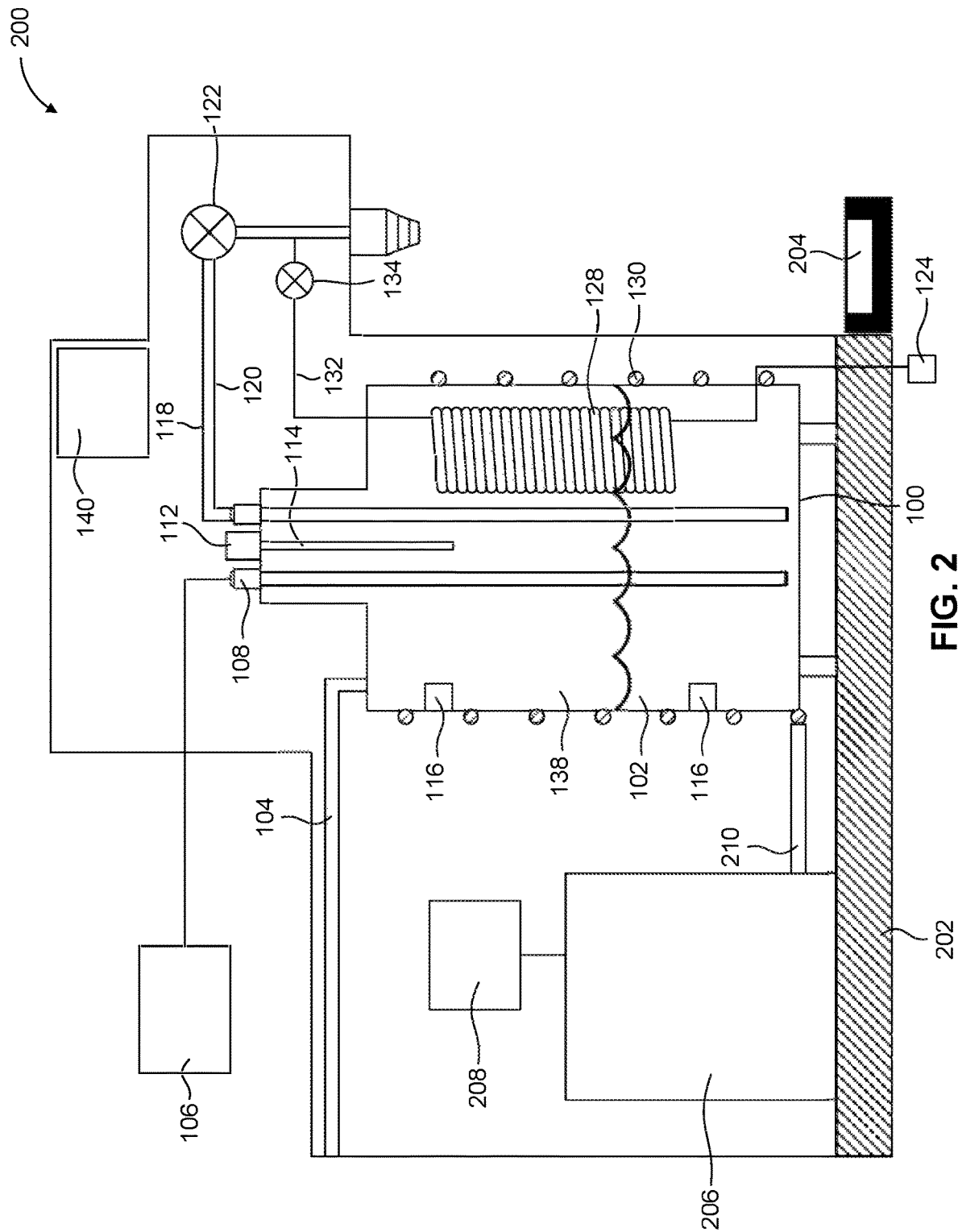
FIG. 2 shows a sectional view of a beverage dispensing system according to some embodiments.
Figure 3:
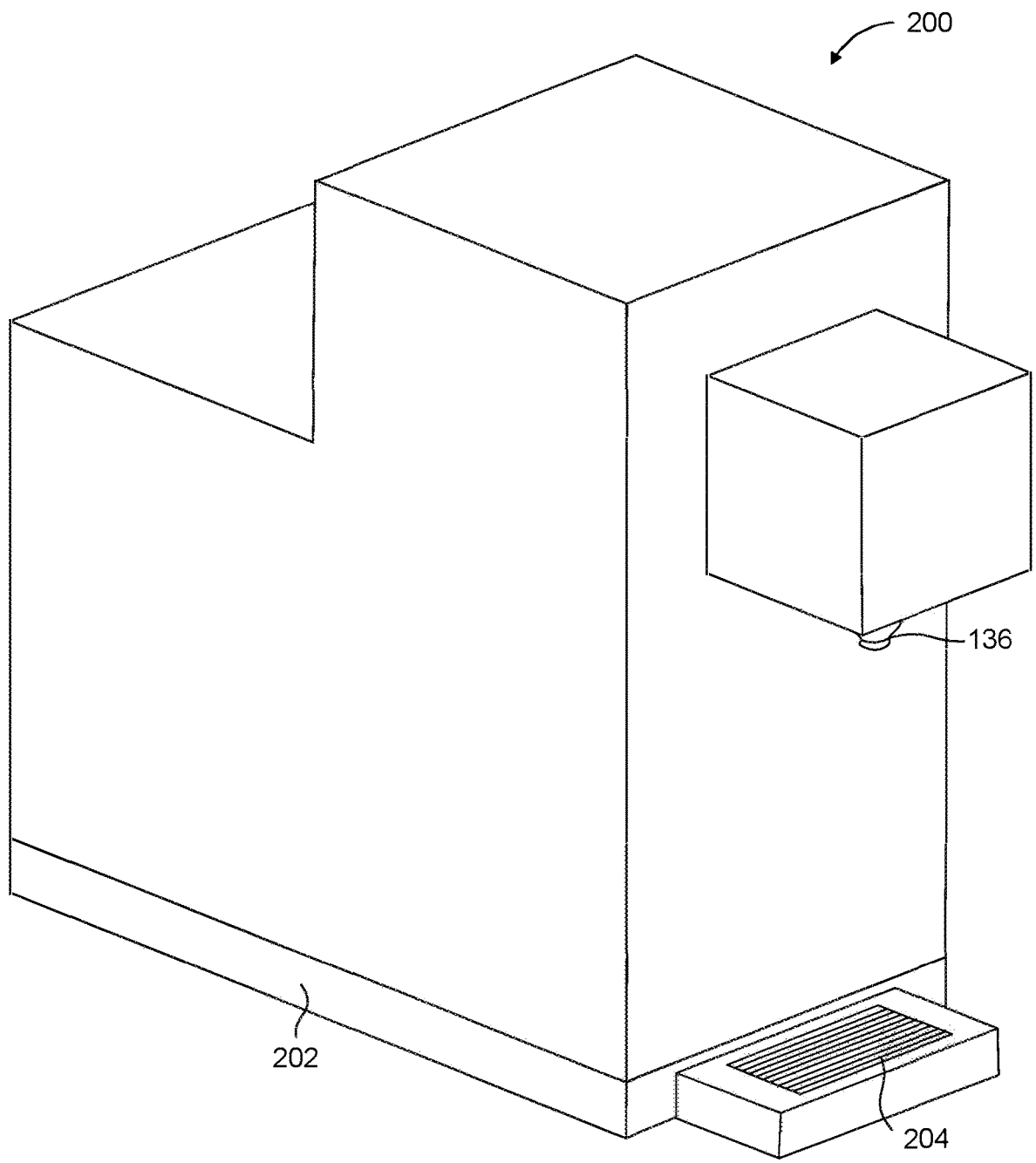
FIG. 3 shows a perspective view of a beverage dispensing system according to some embodiments.

In some embodiments, beverage dispensing system 100 may include a controller 140 for controlling operation of system components with or without additional manual input. Solenoid valve 112 may be operatively coupled to the controller 140 (as shown in FIG. 2). Controller 140 may instruct solenoid valve 112 to open in response system conditions or elapsed time. Controller 140 may also instruct solenoid valve 112 to open in response to a manual instruction. Carbonation input valve 108 may have a plurality of open states. For example, carbonation input valve 108 may have a closed state, open state, and partially open state. In the closed state, carbonation input valve 108 may prevent the flow of gaseous carbon dioxide into tank 101 from carbon dioxide source 106. In the open state, carbonation input valve 108 may allow a maximum rate of transfer of carbon dioxide from carbon dioxide source 106 to tank 108. Carbonation input valve 108 in the open position allows carbon dioxide to flow from carbon dioxide source 106 into tank 101.

Sensors 116 located in tank 101 may monitor the concentration of carbon dioxide in gas 138 or in water 102. Sensors 116 may be electronically coupled to controller 140

(connection not shown). Sensors 116 may report concentration of carbon dioxide information to controller 140.

Sensors 116 may monitor the amount of carbon dioxide directly or indirectly. For example, sensors 116 may determine the amount of carbon dioxide present in gas 138 and determine, using, for example Henry's Law, the amount of carbon dioxide dissolved in water 102. Sensors 116 may also determine the amount of carbon dioxide dissolved in water 102 directly. Sensors 116 may be fully submerged in water 102, partially submerged in water 102, or above water 102 in the space occupied by gas 138. Sensors 116 may be any one of a variety of chemical sensors including, but not limited to, heteropolysiloxane sensors. Sensors 116 may also include temperature sensors to determine the temperature of water 102. Sensors 116 may be located in various positions in tank 101 to determine the amount of carbon dioxide dissolved in water 102.

Tank 101 includes release valve 112 coupled to release pipe 114. Release pipe 114 is fluidly coupled to tank 101 such that gas 138 may flow outside of tank 101 when release valve is open. Release valve 112 may be actuated by controller 140. In some embodiments, the actuation of release valve 112 may be timed to increase the homogeny of the carbon dioxide dissolved in the water. Release valve 112 may be opened in response to a signal from sensors 116. Sensors 116 may indicate that the level of homogeny in either temperature or in carbon dioxide concentrations may be outside of acceptable limits.

In some embodiments, when release valve 112 is opened, gas 138 contained in tank 101 may escape tank 101 through release pipe 114 because gas 138 is at higher pressure than the pressure outside of tank 101.

In some embodiments, the pressure in the space occupied by gas 138 drops as gas 138 escapes from tank 101 through release pipe 114. As the pressure drops, carbon dioxide rushes inside the tank through holes and gets dissolved in water 102. As the carbon dioxide is released from water 102, water 102 is agitated. In some embodiments, the agitation of water 102 increases the homogeny of properties of water 102. For example, in some embodiments, the agitation of water 102 increases the temperature homogeny and the carbon dioxide concentration homogeny.

In some embodiments, release valve 112 may be actuated periodically. For example, release valve may be actuated every 5 minutes. Release valve 112 may also be actuated a delay time after a specified event or sequence of events. For example, release valve 112 may be actuated a delay time after water 104 is added to tank 101 through water pipe 104. In another example, release valve 112 may be actuated a delay time after water 104 is dispensed from tank 101.

In some embodiments, delay time is determined based on other criteria. The other criteria may include, for example, the addition of water 102 or gas 138 to tank 101, the dispensing of water 102 from tank 101, or other event. For example, delay time may begin upon dispensing of a carbonated drink from carbonated drink dispenser 100. In some embodiments, controller 140 receives a signal from water dispensing valve 122 indicating that carbonated water was dispensed from carbonated beverage dispenser 100. In some embodiments, controller 140 may open release valve 112 a specified period of time after controller 140 receives a signal from water dispensing valve 122. Controller 140 may open release valve 112 for an open time. Open time may or may not correspond to the amount of time water dispending valve 122 is open.

In some embodiments, the delay time may be up to 6 seconds. In some embodiments, the delay time is between 0.5 and 6 seconds. In some embodiments, delay time can be programmed into controller 140. Other time delays may be used based on the needs carbonated beverage dispenser 100. For example, the time delay may depend on the amount of carbonated water dispensed from carbonated beverage dispenser 100, the time it takes to dispense a certain amount of carbonated water, or the time to refill carbonation tank 101.

In some embodiments, delay time is determined by controller 140. In some embodiments, controller 140 determines delay time based on gas volume specifications for soda strength (i.e., desired carbonation level). In some embodiments, the longer the time delay, the stronger the soda strength (higher carbonation level). For example, more time passing may allow water to enter or refill tank 110 at the right time so that there is enough time for water to mix with carbon dioxide gas. In some embodiments, the combination of the time delay, the addition of carbon dioxide from carbon dioxide source 106, and the flow rate from water input 104 allows for the carbonated drink to achieve gas volume specifications for soda strength.

For example, when water in the carbonation tank falls below the pre-determined level, delay time may begin. In some embodiments, the time delay is between 0.5-6 seconds (e.g., 4 or 5 seconds). The time delay allows for the proper amount of carbonation of water 102 so that gas volume specifications for soda strength are met.

In some embodiments, carbonated beverage dispenser 100 may further include bag in box 124. In some embodiments, bag in box 124 may contain syrup to add to water 102 as water 102 is dispensed from tank 101. Bag in box 124 may have syrup tube 132 extending therefrom. Syrup tube 132 carries syrup from bag in box 124. Syrup tube 132 may pass through tank 101 and into water 102.

As shown in FIG. 1, syrup may be pumped using pump 126 from bag in box 124 trough syrup tube 132. Syrup tube 132 may have coils 128 in water 102 of tank 101. Coils 128 aid in the transfer of heat from syrup 128 to water 102 by increasing the surface area of syrup exposed to water 102. Thus, as syrup passes through coil 128, it is cooled to a temperature that is, for example, approximately the same as water 102. In this way, syrup may be dispensed from carbonated beverage dispenser 100 at approximately the same temperature as water 102.

A user wishing to dispense a beverage from carbonated beverage dispenser 100 may engage dispensing nozzle 136. Dispensing nozzle 136 may be configured to dispense a mixture of syrup and carbonated water 102 from carbonated beverage dispenser 100.

In some embodiments, tank 101 is cooled by water cooling coils 130. Water cooling coils 130 may be disposed on the outside of tank 101, as shown in FIG. 1 or may be disposed on the interior of tank 101. In some embodiments, water cooling coils 130 provide an elongated path for more surface area for the heat exchange.

In some embodiments, water cooling coils 130 are kept at a cold temperature through the use of a refrigeration system. In some embodiments, water cooling coils 130 are evaporation coils. As shown in FIG. 2, the refrigeration system may include compressor 208 and condenser 206 coupled to cooling/evaporation coils 130 via coolant conduit 210. In some embodiments, cooling/evaporation coils 103 may pass in close proximity to syrup cooling coils 128. In some embodiments, ice may be added to or formed in tank 101. In some embodiments, tank 101 includes a drain (not shown), which may facilitate emptying water tank 101 for cleaning or servicing of components.

FIG. 2 presents a cross sectional view of a carbonated beverage dispenser 100 according to some embodiments. As shown in FIG. 2 carbonated beverage dispenser 100 includes base 202. Base 202 may be weighted to stabilize carbonated beverage dispenser 100. Base 202 may also be configured to mount on, for example, another surface such as a counter, shelf, or in another display unit.

In some embodiments, compressor 208 and condenser 206 are thermally coupled with evaporation coils 130 via thermal coupling 210. Compressor 208, condenser 206, and evaporation coils 130 work to remove heat from tank 101. Heat removed from tank 101 is rejected at condenser 206. Heat may be rejected out of carbonated beverage dispenser 100 to reduce the overall temperature inside of carbonated beverage dispenser 100.

In some embodiments, water 102 may be added to tank 101 inside carbonated beverage dispenser 100 via water pipe 104. Water pipe 104 may be internal to carbonated beverage dispenser 100 but may contain an interface on the exterior of carbonated beverage dispenser 100 to supply water 102 into carbonated beverage dispenser 100. In some embodiments, carbon dioxide source 106 may be interior of carbonated beverage dispenser 200. In some embodiment, carbon dioxide source 106 maybe exterior of carbonated beverage dispenser 200. In some embodiments, carbon dioxide source 106 may be coupled to tank 101 by carbon dioxide source pipe 110. Carbon dioxide source pipe may include carbon dioxide source valve 108 configured to add carbon dioxide into tank 101.

In some embodiments, bag in box 124 may be exterior of beverage dispensing machine 200. For example, bag in box 124 may be below beverage dispensing machine 200 when beverage dispensing machine 200 is placed on a surface, such as a counter. Bag in box 124 may be located near the front of carbonated beverage dispenser 100. Locating bag in box 124 near the front of carbonated beverage dispenser 100 may be advantageous because the front of carbonated beverage dispenser 100 may be more accessible. Therefore, exchanging empty bag in box 124 for full bag in box 124 may be less strenuous. In some embodiments multiple bags in box 124 may be present in carbonated beverage dispenser 100. Multiple bags in box 124 may provide the user with a greater variety of beverage options or flavor additions.

Dispensing nozzle 136 may be located above drip tray 204. Drip tray 204 is configured to collect excess water 102 and syrup dispensed from dispensing nozzle 136. Drip tray 204 may have a closed bottom or may have a drain on the bottom. The drain on the bottom of drip tray 204 may carry way excess water 102 which may drip from dispensing nozzle 136.

Figure 4:
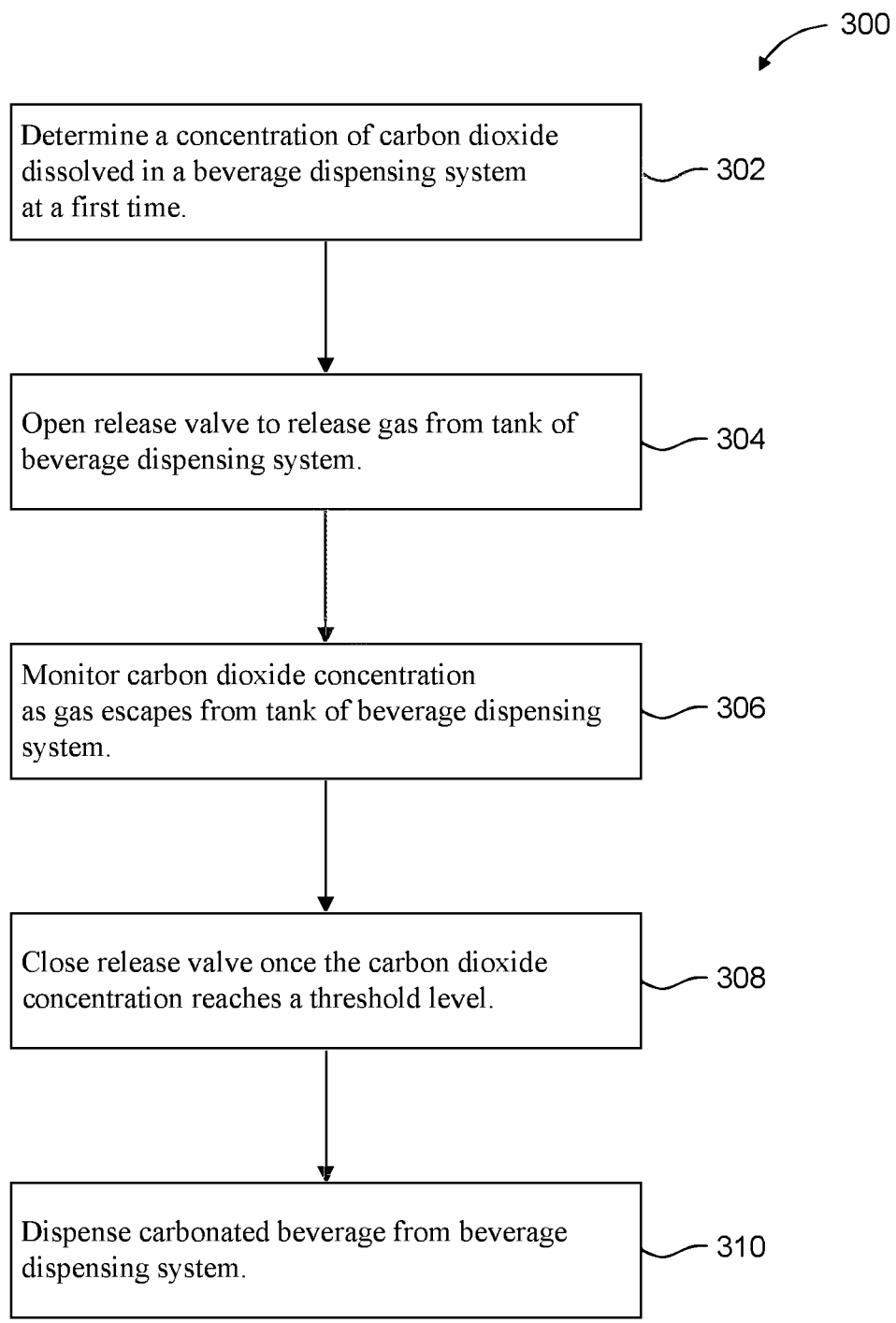
FIG. 4 is a flow chart illustrating a method of dispensing a beverage according to some embodiments.

FIG. 4 shows a method of dispensing a beverage according to an embodiment. A method of dispensing a beverage 300 includes determining a concentration of carbon dioxide dissolved in a beverage dispensing system at a first time 302. Determining a concentration of carbon dioxide dissolved in a beverage dispensing system at a first time 302 may include using sensors 116 as described above. In some embodiments, after determining a concentration of carbon dioxide dissolved in a beverage dispensing system at a first time 302, release valve 112 may be opened 304 to release gas 138 from tank 101. In some embodiments, while release valve 112 is open and gas 138 escapes from tank 101, monitoring 306 of carbon dioxide concentrations may occur.

In some embodiments, release valve 112 may be closed 308 once the level of carbonation in water 102 reaches a threshold level. In some embodiments, method of dispensing a beverage 300 includes dispensing 310 water 102 from carbonated beverage dispenser 100.

In some embodiments, method of dispensing a beverage 300 including adding carbon dioxide to tank 101. In some embodiments, method of dispensing a beverage 300 including adding water 102 to tank 101. Further, in some embodiments, no agitation fan is used to agitate the water.

Various aspects of the present invention, or any parts or functions thereof, may be implemented using hardware, software, firmware, tangible computer readable or computer usable storage media having instructions stored thereon, or a combination thereof, and may be implemented in one or more computer systems or other processing systems. This includes, but is not limited to, controllers for any valves, systems of vales, nozzles, systems of nozzles, and sensing systems.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A carbonated beverage dispensing system, comprising:
   a tank for holding water with carbon dioxide dissolved therein;
   a carbon dioxide source configured to deliver carbon dioxide to the tank;
   a release valve in communication with the tank and configured to release gas from the tank;
   a sensor; and
   a release valve configured to actuate to release gas from the tank in response to a signal received from the sensor.

2. The system of claim 1, wherein release valve is configured to open for an actuation period.

3. The system of claim 1, wherein the release valve is configured to open at a pre-determined delay time after water is added to the tank.

4. The system of claim 1, further comprising a solute source configured to add a solute to the water.

5. The system of claim 4, wherein the solute source comprises a syrup pipe configured to pass through the volume of water.

6. The system of claim 1, wherein the sensor comprises a carbon dioxide sensor configured to determine the level carbon dioxide dissolved in water in the tank.

7. The system of claim 6, further comprising a controller configured to actuate the release valve in response to the carbon dioxide sensor determining that the level of carbon dioxide dissolved in the water is outside of a pre-determined threshold range.

8. The system of claim 7, wherein the controller is configured to actuate the release valve at a pre-determined delay time after a carbonated beverage is dispensed from the tank.

9. The system of claim 7, wherein the controller is configured to actuate the release valve periodically to improve the homogeny of a property of the water.

10. The system of claim 1, wherein
the release valve is further configured to release gas from the tank at a pre-determined delay time after water is added to the tank or after the dispensing valve is actuated.

11. The system of claim 10, wherein the pre-determined delay time is 60 seconds.

12. The system of claim 10, wherein the release valve is configured to release gas from the tank volume for an actuation period to improve the homogeny of a property of the water.

* * * * *

UNITED STATES PATENT AND TRADEMARK OFFICE
CERTIFICATE OF CORRECTION

PATENT NO. : 12,264,057 B2  
APPLICATION NO. : 18/474870  
DATED : April 1, 2025  
INVENTOR(S) : Bhutani et al.

Page 1 of 1

It is certified that error appears in the above-identified patent and that said Letters Patent is hereby corrected as shown below:

In the Claims

In Column 9, Claim 6, Line 10, delete "level" and insert --level of--, therefor.

Signed and Sealed this
Twentieth Day of May, 2025

Coke Morgan Stewart
*Acting Director of the United States Patent and Trademark Office*